US00PP34885P2

(12) United States Plant Patent
Harrison

(10) Patent No.: US PP34,885 P2
(45) Date of Patent: Jan. 3, 2023

(54) ***ABELIA* PLANT NAMED 'RHABPE22'**

(50) Latin Name: *Abelia grandiflora nana.*
Varietal Denomination: 'Rhabpe22'

(71) Applicant: Robert Harrison, Tynong (AU)

(72) Inventor: Robert Harrison, Tynong (AU)

( * ) Notice: Subject to any disclaimer, the term of this patent is extended or adjusted under 35 U.S.C. 154(b) by 0 days.

(21) Appl. No.: 17/894,451

(22) Filed: Aug. 24, 2022

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new cultivar of *Abelia* named 'Rhabpe22' that is distinguishable by dense, compact and mounding plant habit and colorful variegated foliage. In spring and early summer, and in shade, the leaves of 'Rhabpe22' exhibit mid-green centers and contrasting cream-yellow margins. In summer to fall, the leaves of 'Rhabpe22' develop very dark green centers and Rhabpe22-orange margins. In combination, these characteristics. In combination these traits distinguish 'Rhabpe22' from all other varieties of *Abelia* known to the inventor.

2 Drawing Sheets

Genus and species: *Abelia grandiflora nana.*
Variety denomination: 'Rhabpe22'.

BACKGROUND

The present disclosure relates to a new and distinct cultivar of *Abelia* plant, a shrub that is grown for use as an ornamental landscape and container plant. The new variety is known botanically as *Abelia grandiflora nana* and will be referred to hereinafter by the cultivar name 'Rhabpe22'.

'Rhabpe22' was first observed by the inventor as a naturally occurring branch sport which was growing on a single plant of *Abelia grandiflora nana* (species, unnamed, unpatented) in the inventor's nursery in Tynong, Victoria, Australia. *Abelia grandiflora nana* is a compact shrub grown for its non-variegated glossy green foliage. The inventor observed that one of his plants of *Abelia grandiflora nana* had developed a stem which bore striking variegated foliage along its length. In 2015, the inventor took and rooted a small number of softwood cuttings in order to establish the variegated form on its own roots, to evaluate its stability, and to increase numbers for commercial introduction.

The inventor has determined that 'Rhabpe22' is a stable cultivar which reproduces true-to-type in successive generations of asexual reproduction.

SUMMARY

The following traits have been repeatedly observed and represent the distinguishing characteristics of 'Rhabpe22'. 'Rhabpe22' has not been tested under all possible conditions and phenotypic differences may be observed with variations in environmental, climatic, and cultural conditions, without however, any variance in genotype.

1. 'Rhabpe22' exhibits a dense, compact and mounding plant habit.

2. The foliage of 'Rhabpe22' is variegated, with green centers and broad contrasting margins.
3. In spring and early summer, and in shade, the leaves of 'Rhabpe22' exhibit mid-green centers and cream-yellow margins.
4. In summer to fall, in full sun, the leaves of 'Rhabpe22' develop very dark green centers and Rhabpe22-orange margins.

DESCRIPTION OF THE PHOTOGRAPHS

The accompanying color photographs illustrate the overall appearance of the new *Abelia* cultivar 'Rhabpe22' showing the colors as true as it is reasonably possible to obtain in colored reproductions of this type. Photographs were taken in August 2022 in Santa Barbara, Calif. from a two-year-old plant grown outdoors in a 2-gallon container, with one pinch after initial cutting establishment and without any chemical growth regulators. Plants of 'Rhabpe22' have developed their characteristic bronzed or Rhabpe22-colored foliage at this time of year. Colors in the photographs may differ from the color values cited in the detailed botanical description, which more accurately describes the actual colors of the new variety 'Rhabpe22'.

DESCRIPTION OF THE NEW VARIETY

Figure 1:
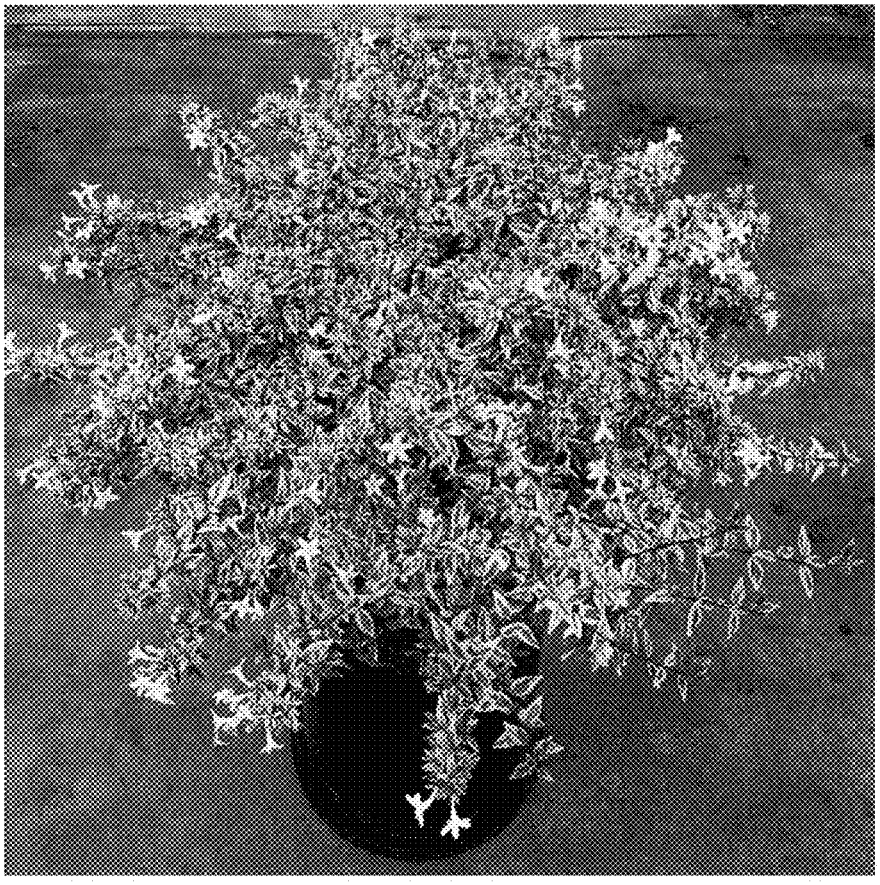
FIG. 1 depicts an entire plant of 'Rhabpe22' in flower in August.
Figure 2:
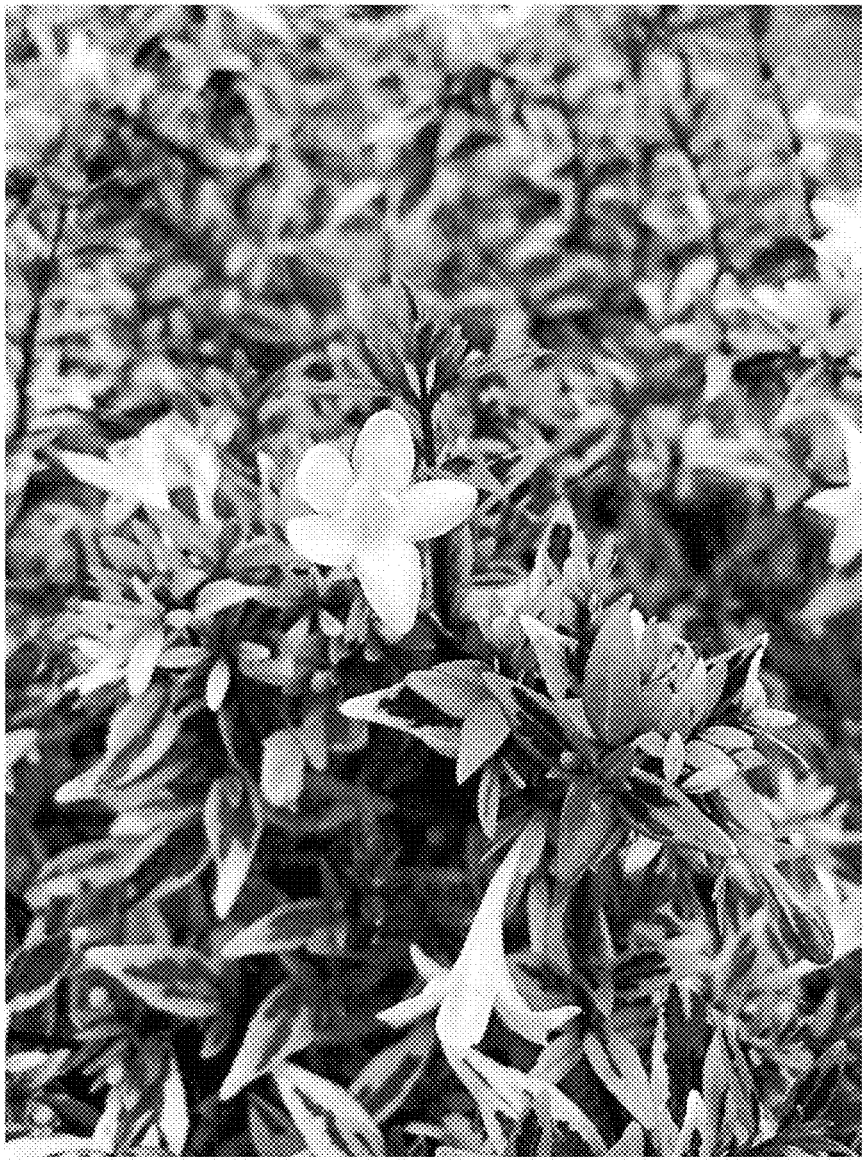
FIG. 2 depicts a close-up view of the foliage and flowers of 'Rhabpe22' in August.

The following detailed descriptions set forth the distinctive characteristics of 'Rhabpe22'. Observations, measurements, values, and comparisons were collected in August 2022 in Santa Barbara, Calif. from an eight months old plant which had been growing outdoors in full sun in a 2-gallon container in Santa Barbara, Calif., with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family.*—Caprifoliaceae.

*Genus.*—*Abelia.*

*Species.*—*grandiflora nana.*

Parentage: Naturally occurring branch sport found on one plant of the species *Abelia grandiflora nana.*

Plant:

*Propagation method.*—Softwood tip cuttings.

*Rooting system.*—Fine and fibrous.

*Vigor.*—Moderate vigor.

*Time to develop roots.*—7-10 days are needed for a cutting to develop roots at recommended rooting temperature of 20° to 22° Centigrade.

*Crop time.*—Approximately 3-4 months are required to produce a full plant in a quart container, and approximately 6-8 months in a 1 gallon container.

*Suggested container size.*—Quart to one-gallon container.

*Use.*—Ornamental shrub which is colorful year-round in the landscape or in planted containers.

*Type, hardiness.*—Evergreen in USDA Hardiness Zones 7 and above. Semi-deciduous in Zone 6.

*Overall dimensions.*—After eight months growth in a 2-gallon container, 25 cm-30 cm in height, and 30 cm in width.

*Cultural requirements.*—Propagate cuttings and grow young plants in semi-shade. Established plants may be grown in full sun with moderate water and well-draining soil.

*Form.*—Mounding and spreading with lightly arching branches.

*Growth habit.*—Dense, compact.

*Blooming season.*—From early summer to fall.

Stems (below first pinch):

*Condition.*—Lignified.

*Bark.*—Papery and semi-glossy.

*Shape.*—Terete.

*Length.*—1 cm to 2 cm.

*Diameter.*—4 mm.

*Bark color.*—199C.

*Texture.*—Rough.

Branches:

*Quantity.*—Approximately 40, of which 8-10 are primary branches and 30 or more are secondary branches.

*Shape.*—Terete.

*Primary branch dimensions.*—17 cm in length, 3-4 mm in diameter.

*Secondary branch dimensions.*—9 cm in length, 1.0 mm-1.5 mm in diameter.

*Internode length* (*all branches*).—15 mm-18 mm.

*Branch color.*—Older growth of primary branches, lignified as stem, color 199C, surface rough. New growth of primary branches, and all growth of secondary branches, color between 60A and 53A, surface smooth, glabrous.

Leaves:

*Type.*—Simple, evergreen or semi-deciduous.

*Variegation.*—Leaves predominantly bicolored with green centers and broad cream-yellow or orange margins which extend by 2 mm-4 mm.

*Arrangement.*—Opposite pairs.

*Attachment.*—Short petiolate.

*Quantity per branch.*—6 to 8 pairs.

*Shape.*—Lanceolate on emergence, Ovate when mature.

*Length.*—Up to 25 mm.

*Width.*—Up to 10 mm.

*Margin.*—Juvenile foliage, entire; mature foliage, lightly crenate, 2-3 shallow rounded notches approximately 0.5 mm in depth and width.

*Thickness.*—Medium.

*Venation.*—Pinnate, barely visible except midrib prominently raised on abaxial surface.

*Vein colors* (*both surfaces*).—As adjacent leaf lamina except abaxial midrib 138C.

*Leaf texture.*—Smooth and glabrous, glossy adaxial surface, semi-glossy abaxial surface.

*Leaf colors* (*newly emerging foliage and foliage shaded from direct sun*).—Adaxial surface: center 141B, margin 3B-3D. Abaxial surface: center 138C, margin 155A.

*Leaf colors* (*mature foliage growing in direct sun*).—Adaxial surface: center N189A, margin initially 32A becoming 31B. Abaxial surface: center 137D, margin 26D.

*Leaf colors* (*occasional non-variegated leaves*).—Adaxial surface: 31B. Abaxial surface: 26D.

*Apex.*—Acute.

*Base.*—Rounded.

*Fragrance.*—None.

Petiole:

*Shape.*—Sulcate.

*Length.*—1.5 mm-2.0 mm.

*Width.*—1.0 mm.

*Texture.*—Smooth, glabrous.

*Color* (*older leaves*).—174C.

*Color* (*new growth*).—53A.

Inflorescence (solitary flowers):

*Type.*—Solitary funnelform five-petaled flowers borne on short peduncles (no pedicels) in leaf axils.

*Quantity per branch* (*where present*).—1-6.

*Quantity per plant.*—Approximately 50.

*Flower depth* (*including corolla tube*).—18 mm.

*Flower diameter* (*across petal apices, fully expanded*) .—15 mm.

*Flower aspect.*—Outward facing, horizontal or upright.

*Fragrance.*—None.

*Lastingness and persistence of flowers.*—3-4 days once fully open, self-cleaning.

Peduncle:

*Length.*—5 mm.

*Shape.*—Terete.

*Diameter.*—1.5 mm-2.0 mm.

*Texture.*—Smooth, lightly puberulent.

*Color* (*bud and emerging flower*).—38D.

*Color* (*flower fully open*).—Between 38D and N155C.

Calyx:

*Shape.*—Stellate.

*Height.*—4 mm.

*Diameter across sepal apices.*—6 mm.

Sepals:

*Quantity.*—5, basally fused.

*Length.*—7 mm.

*Width.*—2.5 mm.

*Shape.*—Oblanceolate.

*Apex.*—Acute.

*Base.*—Truncate.

*Margin.*—Entire.

*Texture* (*both surfaces*).—Smooth, very lightly puberulent.

*Color* (*both surfaces*).—38D.

Bud:

*Shape.*—Club-shaped.

*Color.*—59D with longitudinal stripes N155C.

*Bud surface.*—Puberulent.

*Bud dimensions.*—15 mm. in length and 4 mm-5 mm. in diameter.

Corolla:

*Corolla tube dimensions.*—12 mm. in length and 3 mm-4 mm. in diameter.

*Corolla tube surface* (*inner surface*).—Pubescent.

*Corolla tube surface* (*outer surface*).—Glabrous.

*Corolla tube color* (*both surfaces*).—N155B.

Petals:

*Petals.*—Five in number, basally fused, free orbicular lobes.

*Petal aspect.*—Gently recurved.

*Petal length.*—18 mm., of which 4.5 mm fused.

*Petal lobe width.*—4 mm.

*Petal surface* (*adaxial surface*).—Pubescent, hairs very fine, white NN155D, up to 1 mm. in length.

*Petal surface* (*abaxial surface*).—Glabrous.

*Petal color* (*both surfaces*).—Flower opening, N155B; flower fully expanded NN155D.

*Petal apex.*—Rounded.

*Petal base.*—Truncate.

*Petal margins.*—Entire.

Reproductive organs:

*Stamens.*—Quantity: 4. Filaments: Free, length 14 mm-15 mm, diameter 0.5 mm. Color: NN155D-N155B.

*Anthers.*—Shape: Ellipsoid, basally attached. Dimensions: 1.5 mm in length, 0.5 mm in width. Color: 155A.

*Pollen.*—None.

*Pistil.*—Quantity: 1. Style: 15 mm-16 mm in length, 0.5 mm in diameter.

*Stigma.*—Position: Held approximately 4 mm above anthers. Shape, dimensions: Flattened globe, 1.5 mm in height, 2 mm in diameter. Color: NN155A.

*Ovary.*—Not observed.

Seed: None.

Disease and pest susceptibility: Susceptible to aphids (*Aphis gossypii*) when stressed. Generally outgrows most bacterial diseases.

Heat, humidity and drought tolerance: Very tolerant of full sun and high humidity when established in the landscape or planted in well-watered containers. Moderate drought tolerance.

COMPARISON WITH PARENTAL LINES AND KNOWN VARIETY

In comparison with the species parent, 'Rhabpe22' exhibits variegated foliage. The parent plant, *Abelia grandiflora nana* bears entirely non-variegated foliage. The overall plant form and the flowers of 'Rhabpe22' and *Abelia grandiflora nana* are very similar.

The closest variety of variegated *Abelia* known to the inventor is *Abelia* Plant Named 'Kaleidoscope' (U.S. Plant Pat. No. 16,988). Both 'Kaleidoscope' and 'Rhabpe22' bear colorful variegated foliage. However, the foliage of 'Kaleidoscope' ranges through several colors from golden yellow to bright scarlet-red in summer and fall, and the foliage of 'Rhabpe22' is predominantly orange in color and does not develop bright red fall coloration. In addition, the overall size of plants of 'Kaleidoscope' are considerably larger, increasing with age. A mature plant of 'Kaleidoscope' will be approximately twice the size (height and diameter) of a same-aged plant of 'Rhabpe22'.

I claim:

1. A new and distinct cultivar of *Abelia* plant named 'Rhabpe22' as described and illustrated herein.

* * * * *